US006821954B2

(12) United States Patent
Reid et al.

(10) Patent No.: US 6,821,954 B2
(45) Date of Patent: Nov. 23, 2004

(54) COMPOUNDS AND USES THEREOF IN TREATING BONE DISORDERS

(75) Inventors: Ian Reginald Reid, Auckland (NZ); Jillian Cornish, Auckland (NZ); Garth James Smith Cooper, Auckland (NZ); David H Coy, New Orleans, LA (US)

(73) Assignee: Auckland UniServices Limited (NZ)

( * ) Notice: Subject to any disclaimer, the term of this patent is extended or adjusted under 35 U.S.C. 154(b) by 0 days.

(21) Appl. No.: 09/875,571

(22) Filed: Jun. 5, 2001

(65) Prior Publication Data

US 2003/0064918 A1 Apr. 3, 2003

Related U.S. Application Data

(63) Continuation of application No. 08/933,452, filed on Sep. 18, 1997, now abandoned.

(51) Int. Cl.$^7$ .......................... A61K 38/08; C07K 7/06
(52) U.S. Cl. ........................................ 514/16; 530/328
(58) Field of Search ............................ 514/16, 17, 12; 530/324, 328, 329

(56) References Cited

U.S. PATENT DOCUMENTS 5,405,831 A * 4/1995 MacIntyre ..................... 514/4

FOREIGN PATENT DOCUMENTS

| AU | A-21575/88 | 7/1989 | | |
| EP | 289287 A2 * | 11/1988 | .......... | A61K/37/02 |
| WO | WO 88/02863 | 4/1988 | | |
| WO | WO 9602269 A1 * | 2/1996 | .......... | A61K/38/17 |

OTHER PUBLICATIONS

Feit et al., "Inherency in Patent Law" (Jan., 2003) J. Pat. Trademark Off., 85(1), 5–21.*
Cornish et al., "Amylin Stimulates Osteoblast Proliferation and Increases Mineralized Bone Volume in Adult Mice" (1995) Biochem. Biophys. Res. Comm., 207(1) 133–139.*
Calcif. Tissue Int. vol. 56, pp. 54–61. D. F. Romero et al., "Amylin Increases Bone Volume but Cannot Amelionate Diabetic Ostoperia".
Endocrine Reviews, vol. 15, No. 2, pp. 163–201. Cooper, G.J.S. "Amylin Compared with Calcitonin Gene–Related Peptide: Structure, Biology, and Relevance in Metabolic Disease".
Bone, vol. 14, pp. 167–172, Pietschmann, P. et al., Inhibitory Effect of Amylin on Basal and Parathyroid Hormone–Stimulated Bone Resorption in Cultured Neonatal MouseCalvaria.
Trends in Endocrinology and Metabolism, vol. 4, No. 8, pp. 255–259. Mone Zaidi et al. "Amylin in Bone Conservation: Current Evidence and Hypothetical Considerations".
J. Cellular Physiology vol. 153, pp. 6–14. Tamura, T., et al "Mechanism of Action of Amylin in Bone".
Biochem. Biophys. Res. Comm. vol. 162, No. 2, pp. 876–881. Datta, H.K. et al "In vivo and in vitro effects of amylin and amylin–amide on calcium metabolism in the rat and rabbit".
Proc. Nat. Acad. Sci. USA, vol. 184, pp. 8628–8632. Cooper, G.J.S. et al "Purification and characterisation of a peptide from amyloid–rich pancreases of Type 2 diabetic patients".

(List continued on next page.)

Primary Examiner—Jon P. Weber
(74) Attorney, Agent, or Firm—Fish & Richardson P.C.

(57) ABSTRACT

A compound derived from amylin is disclosed. Pharmaceutical compositions contain such compounds and are used in the treatment of bone disorders where stimulation of bone growth is required.

20 Claims, 9 Drawing Sheets

OTHER PUBLICATIONS

Experimental Physiology, vol. 78, pp. 183–196. A.S.M. Towdihul Alam et al "Amylin Inhibits Bone Resorption by a Direct Effect on the Motility of Rat Osteoclasts".

J. Bone Miner. Research vol. 15, S229, Abstract 621. Datta, H.K. et al "Amylin–amide competes with CGRP binding sites on osteoblast–like osteosarcoma cells".

J. Bone Miner. Research vol. 7, No. 9, pp. 1113–1116. Wimala Wansa, S.J. et al "Hypocalcemic Actions of Amylin Amide in Humans".

American Physiological Society, pp. E9–E15. I.R. Reid et al "Parathyroid hormone depresses cytosolic pH and DNA synthesis in osteoblast–like cells".

Biochemical Society Transactions, vol. 18, p. 1276. Harish Datta et al "Amylin–amide displays a proliferative effect on human umbilical vein endothelial cells".

Calif. Tissu. Int. 50 (Suppl. 1). Tatsuya Tamura et al "Mechanism of Action of Amylin in Osteoclasis and Osteoblasts", (Abstract).

Cornish et al., "Dissociation of Amylin's Effects on Bone Formation and Bone Resorption," Australia and New Zealand Bone and Mineral Society, Annual Scientific Meeting, Sydney, Oct. 1996.

* cited by examiner

COMPOUNDS AND USES THEREOF IN TREATING BONE DISORDERS

CROSS-REFERENCE TO RELATED APPLICATIONS

This is a continuation application of U.S. patent application Ser. No. 08/933,452, filed Sep. 18, 1997 now abandoned, the contents of which are incorporated herein by reference.

TECHNICAL FIELD

This invention relates to novel compounds derived from amylin. The invention also relates to pharmaceutical compositions containing such compounds and their use in the treatment of bone disorders where stimulation of bone growth is required.

BACKGROUND OF THE INVENTION

Amylin is a 37-amino acid peptide co-secreted with insulin from the beta cells of the pancreatic islets. It is structurally related to calcitonin gene-related peptide (CGRP) and more distantly to calcitonin itself. As a result of these similarities and the fact that calcitonin has potent effects on osteoclasts, the actions of amylin in bone have been studied. Amylin mimics some of the effects of calcitonin on bone resorption. It stimulates cyclic AMP formation and induces quiescence in osteoclasts, reducing the amount of bone resorbed. Similar effects are demonstrable in bone culture.

Amylin was first reported by Cooper et al in Proceedings of the National Academy of Sciences USA 84, 8628 (1987) and is the subject of European Patent 289287.

```
Lys-Cys-Asn-Thr-Ala-Thr-Cys-Ala-Thr-Gln-
1                 5                    10

Arg-Leu-Ala-Asn-Phe-Leu-Val-His-Ser-Ser-
11               15                   20

Asn-Asn-Phe-Gly-Ala-Ile-Leu-Ser-Ser-Thr-
21               25                   30

Asn-Val-Gly-Ser-Asn-Thr-Tyr  (SEQ ID NO:1)
31               35
```

The native molecule contains a disulphide bridge between the cysteine residues shown at positions 2 and 7 in the primary structure. Further, it is amidated at the 3'-end and it is formed as a propeptide.

European Patent 289287 reports a number of novel biological effects including enhancement of hepatic glucose output, increased production of lactate from skeletal muscle and reduced action of insulin in skeletal muscle.

Amylin is also reported in European Patent 408284 as having value for treatment of bone disorders and calcium imbalance. The patent specification attributes the activity of amylin to an inhibition of osteoclast motility.

The use of amylin and amylin agonists for the stimulation of bone growth is described and claimed in our related patent application PCT NZ 95/00062 (published as WO 96/62269).

Amylin has been found to affect osteoblasts. There is a dose-dependent stimulation of osteoblast proliferation by amylin in concentrations as low as $10^{-11}$M. Histomorphometric indices of bone formation are increased in vivo following local injection of the peptide. The anti-osteoclastic potency of amylin is substantially reduced in the absence of the carboxyl terminal amide group.

However, details of the structure-activity relationships for the bone effects of amylin are unclear. The actions of amylin to stimulate bone formation and inhibit bone resorption make it an attractive candidate for the therapy of osteoporosis and for the promotion of the repair of local bone defects. The full peptide would be expensive to manufacture, not be active orally, and might have deleterious effects on carbohydrate metabolism.

Amylin has been implicated in the pathogenesis of type 2 diabetes, in part, as a result of amyloid deposition in the pancreatic islets. However, the action of amylin on carbohydrate metabolism requires the intact peptide. Its propensity to form amyloid is dependent, in part, on the amino acids between positions 25 and 29. Thus a peptide that exhibits osteoblast proliferative effects and which has no effect on carbohydrate metabolism or a tendency to lead to amyloid formation is highly desirable as a stimulant of bone formation in the management of osteoporosis and other bone disorders.

DISCLOSURE OF THE INVENTION

While intact amylin produces the greatest maximal effect on osteoblast proliferation, we have now surprisingly found that N-terminal amylin-(1–8), also stimulates osteoblast proliferation, without the effects on carbohydrate metabolism or a tendency to lead to amyloid formation possessed by the whole peptide.

The invention provides compounds which are useful for stimulating bone growth in an animal and is useful for preventing bone deterioration in an animal.

The invention also provides a pharmaceutical composition containing such compounds together with a pharmaceutically acceptable carrier preferably in orally administrable form.

The compounds of this invention are those of formula I.

where $R_1$ is absent, Lys or a functionally effective group and $R_2$ is absent, or Ala or a functionally effective group; or a functionally effective derivative thereof.

The invention also provides a method of stimulating bone growth comprising subjecting bone to the effect of an effective amount of a compound of formula I.

The method of the invention will be particularly useful for treatment of osteoporosis of any cause, bone loss or malignancy, or endocrine disorders or immobility and disuse and in fractures by enabling the patient to reverse previous bone loss. The method can be used for treatment of bone disorders in all animals e.g., mammals particularly humans, cattle, horses, dogs and cats.

The invention further provides a method of prophylactically increasing or maintaining bone density in a subject having a substantially normal bone density comprising the step of administering an effective amount of the amylin fragment.

By this aspect of the invention it is envisaged that patients at risk of bone deterioration will be given a regular dose of the amylin fragment to prevent likely bone deterioration. Patients at most risk are post menopausal women, usually at age above 50, and men over 60 years of age.

Administration within the scope of the invention can also be after bone density has deteriorated beyond the normal level. Normal bone density means bone density within two standard deviations of the mean value for race, age and sex. In view of the effect of inhibiting osteoclast activity and the effect of stimulating bone growth, treatment with the amylin fragment is capable of reversing bone loss.

The compounds of this invention are the 2 to 7 amino acids of amylin with a disulphide bond between the 2 and 7 cysteine groups. Amylin (1–8) is active while amylin (1–8) with 2 to 7 disulphide bond removed is inactive and blocks the activity of amylin (1–8). The 2 to 7 disulphide bond is therefore necessary for osteoblast proliferation.

The N-terminal group $R_1$ can be absent but is preferably lyseine. Functionally effective groups as $R_1$ include derivatives of the N-terminus eg acid addition salts and one or more alternative amino acids and derivatives thereof in which the compound has osteoblast stimulating activity. Similarly the C-terminal group $R_2$ can be absent but is preferably alanine and is preferably amidated. Functionally effective groups as $R_2$ include derivatives such as amides and one or more alternative amino acids and derivative thereof where the compound has osteoblast stimulating activity without an effect on carbohydrate metabolism or a tendency to lead to amyloid formation.

Functionally effective derivatives of the compounds of formula I include agonists and related peptides in which one or more of the 2 to 7 amino acids are replaced by other amino acids and which stimulate osteoblast activity without an effect on carbohydrate metabolism or a tendency to lead to amyloid formation.

The compounds of the invention can be produced by known methods but are preferably synthesised using standard solid phase peptide synthesis techniques. For example, the compounds can be prepared on methylbenzyhydrylamine resin followed by hydrogen fluoride deprotection and cleavage from the resin.

For use in therapy, the compounds can be utilised by themselves or as functionally effective derivatives. The compounds have amine groups which can form salts in accordance with the invention. All the compounds have at least one amino group which will be capable of forming a salt. Where two or more amino groups are present in the compound, the possibility of mixed salts exists which are also within the scope of the invention.

The compounds can be used in the form of a salt with an acid. Acids which can be used preferably include compatible inorganic acids such as hydrochloric and organic acids (or salts thereof) more preferably those occurring in living organisms, including but not limited to oxalic acid, glucuronic acid, pyruvic acid, lactic acid, citric acid, isocitric acid, ketoglutaric acid, succinic acid, malic acid, and oxaloacetic acid. In the preferred case of an aqueous solution, the desired anion can be added either as the free acid, or a salt, preferably one which is highly soluble in water, for example the sodium or potassium salts, but also the lithium, magnesium, calcium or ammonium salts. Moreover, these salts can be used either in anhydrous or hydrated forms. For example citric acid can be used as the anhydrous free acid, the monohydrate free acid, the anhydrous trisodium salt, or the dihydrate trisodium salt. These salts can be prepared by the methods described in WO 96/02269. The compounds can also be amidated at the C-terminal end.

It is desirable that all trifluoroacetic acid or other bone inhibitory acetic acid anions be removed or alternatively be present in such minor amounts as to have no therapeutic effect.

The compounds of the invention can be formulated into pharmaceutical compositions in the normal way to make oral, intranasal or parenteral formulations dependent upon the desired form of administration of the substance. Preferably the compounds can be formulated in orally administrable form eg as tablets, capsules suspensions, syrups and the like.

The compound is administered in an amount to meet the particular condition under treatment. It will be administered to the mammal either injectably, intranasally or in an oral formulation in a form for ensuring the availability of the compound at the particular site for effective therapy. The compounds of this invention are expected to be effective orally.

Parenteral administration can also be employed, either subcutaneously or intramuscularly. For the treatment of fractures or other localised bone disorders, application of the compound directly to the site may be desirable, for example, by injection or by application during surgery. It is believed that the dosage administered will lie within the range 0.01–100 mg/kg of body weight. The actual dose administered to each patient will depend on the type of patient and the nature of the disorder being treated. It is envisaged that for prophylactic therapy the dose will be lower than that required for reversal of bone resorption or treatment of fractures.

Administration of two or more compounds according to the invention, is within the scope of the invention as is the use of a compound of the invention with any other effective therapeutic agent (e.g., calcitonin) including any other agent for treatment of bone disorders. Combination agent therapy can be by separate administration of the individual agents or by combining the two or more agents into one composition form.

The invention will now be described by way of example with reference to the accompanying drawings in which.

METHODS

Osteoblast-Like Cell Culture

Osteoblasts were isolated by collagenase-digestion from 20-day fetal rat calvariae. Calvariae were dissected aseptically and the frontal and parietal bones were stripped of their periosteum. only the central portions of the bones, free from sutrue tissue, were collected. The calvariae were treated twice with phosphate buffered saline (PBS) containing 3 mM EDTA (pH 7.4) for 15 minutes at $37_E$ C. in a shaking water bath. After washing once in PBS, the calvariae were treated twice with 3 ml of 1 mg/ml collagenase for 7 minutes at $37_E$ C. After discarding the supernatants from digestions I and II, the calvariae were treated a further twice with 3 ml of 2 mg/ml collagenase (30 mins, $37_E$ C.). The supernatants of digestions III and IV were pooled, centrifuged, and the cells washed in Dulbecco's modified Eagle's medium (DME) with 10% fetal calf serum (FCS), suspended in further DME/10% FCS and placed in 75 cm² flasks. The cells were incubated under 5% $CO_2$ and 95% air at $37_E$ C. Confluence was reached by 5–6 days, at which time the cells were subcultured. After trypsinization using trypsin-EDTA (0.05%/0.53 mM), the cells were rinsed in minimum essential medium (MEM) with 5% FCS and resuspended in fresh medium, the seeded at $5\times10^4$ cells/ml in 24-well plates (0.5 ml cell suspension per well, i.e. $2.5\times10^4$ cells/well). The osteoblast-like character of these cells has been established by demonstration of high levels of alkaline phosphatase activity and osteocalcin production and a sensitive adenylate cyclase response to parathyroid hormone and prostaglandins.

Proliferation studies (cell counts and thymidine incorporation) were performed in subconfluent cell populations, 24 h after subculturing cells were changed to serum-free medium with 0.1% bovine serum albumin plus the experimental compounds. Cell numbers were analysed 24 hours after addition of the peptide or vehicle by detaching cells form the wells by exposure to trypsin/EDTA (0.05%/0.53 mM) for approximately 5 minutes at $37_E$ C. Counting was performed in a hemocytometer chamber. Results are expressed per well. [$^3$H]-Thymidine incorporation into actively-growing and growth-arrested cells was assessed by pulsing the cells with [$^3$H]-thymidine (0.5 Ci/well) two hours before the end of the experimental incubation. Experiments were terminated at 24 hours by washing the cells in MEM followed by the addition of 10% trichloroacetic acid. The precipitate was washed twice with ethanol:ether (3:1) and the wells desiccated at room temperature. The residue was redissolved in 2 M KOH at $55_E$ C. for 30 mins, neutralized with 1 M HCI, and an aliquot counted for radioactivity. Results are expressed as dpm per well. For cell counts and thymidine incorporation, each experiment was performed at least four different times using experimental groups consisting of at least six wells.

Bone Organ Culture

Bone resorption studies were carried out in neonatal mouse calvariae as described previously. Mice were injected subcutaneously with 5 $Ci^{45}Ca$ at 2 days of age, and hemicalvariae were dissected out four days later. Hemicalvariae were pre-incubated for 24 hours in medium 199 with 0.1% bovine serum albumin, then changed to fresh medium containing peptide or vehicle. Incubation was continued for a further 48 hours. There were 5–7 hemicalvariae in each group.

To determine whether the various peptide fragments underwent significant catabolism in organ culture, they were incubated with calvariae before being added to osteoblast cultures. The organ cultures were set up using hemicalvariae before being added to osteoblast cultures. The organ cultures were set up using hemicalvariae from animals that had not be pretreated with $^{45}Ca$. The fragments or vehicle were incubated with the calvariae for 2, 4, or 6 hours. Extracts of the media were removed then immediately added to osteoblast cultures for measurement of their effects on osteoblast proliferation, as described above.

Materials

The rat amylin-(1–8) and rat amylin-(8–37) employed in this study were C-terminal amides synthesized on methylbenzhydrylamine resin by standard solid-phase techniques followed by hydrogen fluoride deprotection and cleavage from the resin. Amylin-(1–8) was cyclized in a dilute solution of 90% acetic acid by treatment with methanol solutions of iodine and purified to >96% homogeneity by reversed-phase high performance liquid chromatography (RP HPLC). Structures were confirmed by matrix-assisted laser desorption ionization time-of-flight mass spectrometry (MALDI-TOF system, model G2025 A, Hewlett Package Ca, USA) and quantitative amino acid analysis of acid hydrolysates. Rat amylin and amylin (1–8) were reduced in 6M guanidine hydrochloride/0.2 M Tris, pH 8.0/3 mM NaEDTA by the addition (to 20 mM) of dithiothreitol, shaking for 3 h at $4_E$ C., then repurified by RP HPLC (Brownlee C18, 5 micron, 220×2.1 mm column). The buffers were; buffer A, 0.08% TFA, buffer B, 80% acetonitrile in 0.08% TFA and the ramp conditions were (10–80)% over 30 minutes. The reduced peptides were collected, freeze dried and stored under argon at $-20_E$ C. until used. Completeness of reduction was confirmed by the expected alteration in $R_f$ value on RP-HPLC, and by MALDI-TOF MS. Deamidated amylin was purchased from Peninsula Laboratories, Belmont Calif.

EDTA and collagenase were obtained from Sigma Chemical Co., St. Louis, Mo. Trypsin-EDTA, MEM, DME medium, Medium 199 and FCS were from Gibco Laboratories, Grand Island, N.Y. [$^3$H]-thymidine and $^{45}Ca$ chloride were from Amersham International, Buckinghamshire, England.

Statistical Analysis

Data are presented as mean"sem. The significance of differences between groups was determined using Student's t test. The comparisons to be made in each experiment were specified a priori, so no adjustment for multiple comparisons was necessary. Where several experiments have been shown in one figure, the data are expressed as the ratio of results in treatment groups to those in the control group and the 'p' values shown were calculated using the data from the individual experiments, before the data were pooled.

Results

Osteoblasts

Figure 1:
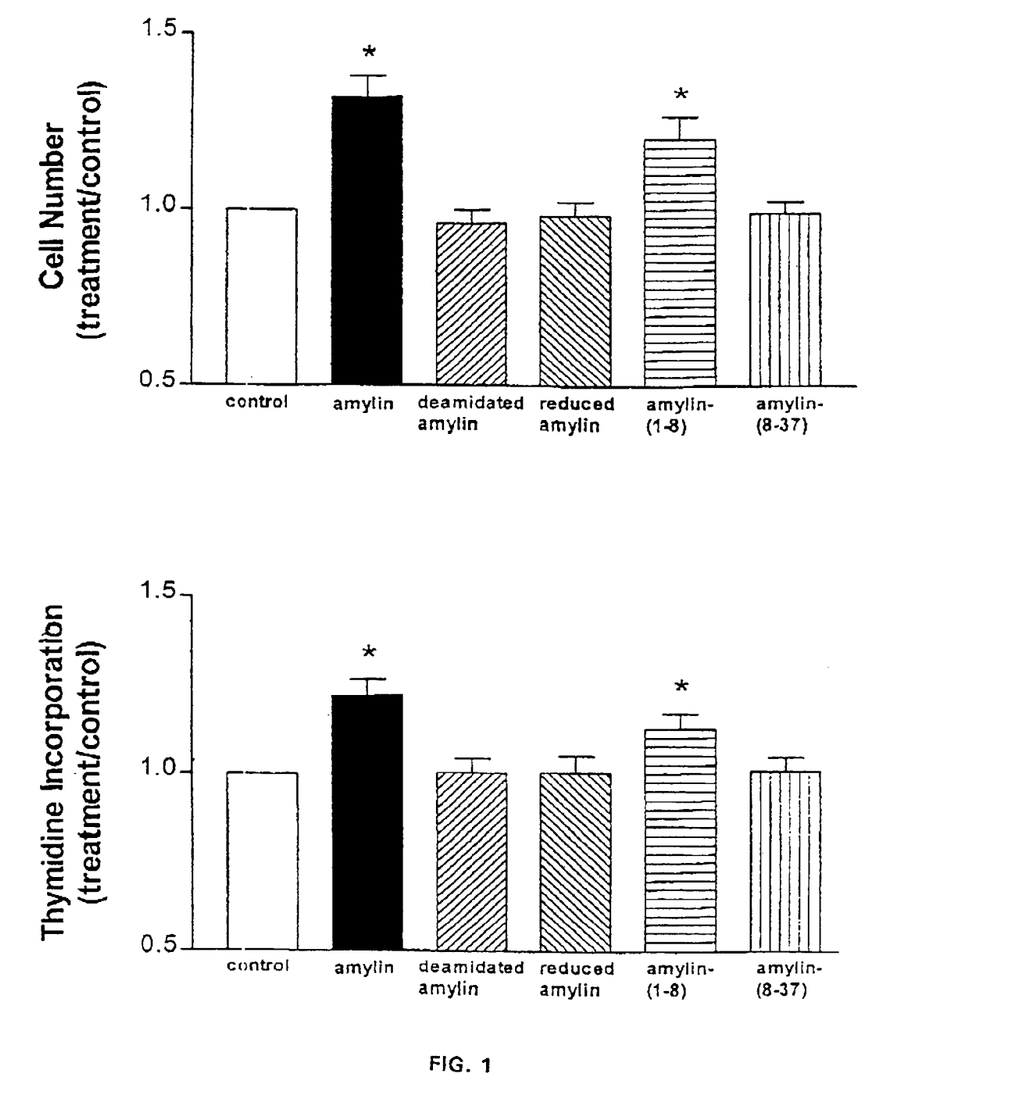
FIG. 1 Effect of equimolar concentrations ($10^{-9}$M) of rat amylin fragments or vehicle on cell number and thymidine incorporation in cultures of fetal rat osteoblasts. Data are expressed as a ratio of treatment to control and are mean"sem.*=significantly different from control, $p<0.002$.

The effects of amylin and its fragments were assessed on both the number of osteoblasts present after a 24 hour incubation and on the thymidine incorporation over the last two hours of this incubation period (FIG. 1). Intact amylin produced a significant increase in cell number and thymidine incorporation. The (1–8) fragment also stimulated both indices, its effect not being significantly different from that of the parent molecule. The other three peptides studied had no effect on osteoblast cell number or thymidine incorporation. Reduced amylin (1–8) like the reduced full molecule, also had no proliferative effect on osteoblasts.

Figure 2:
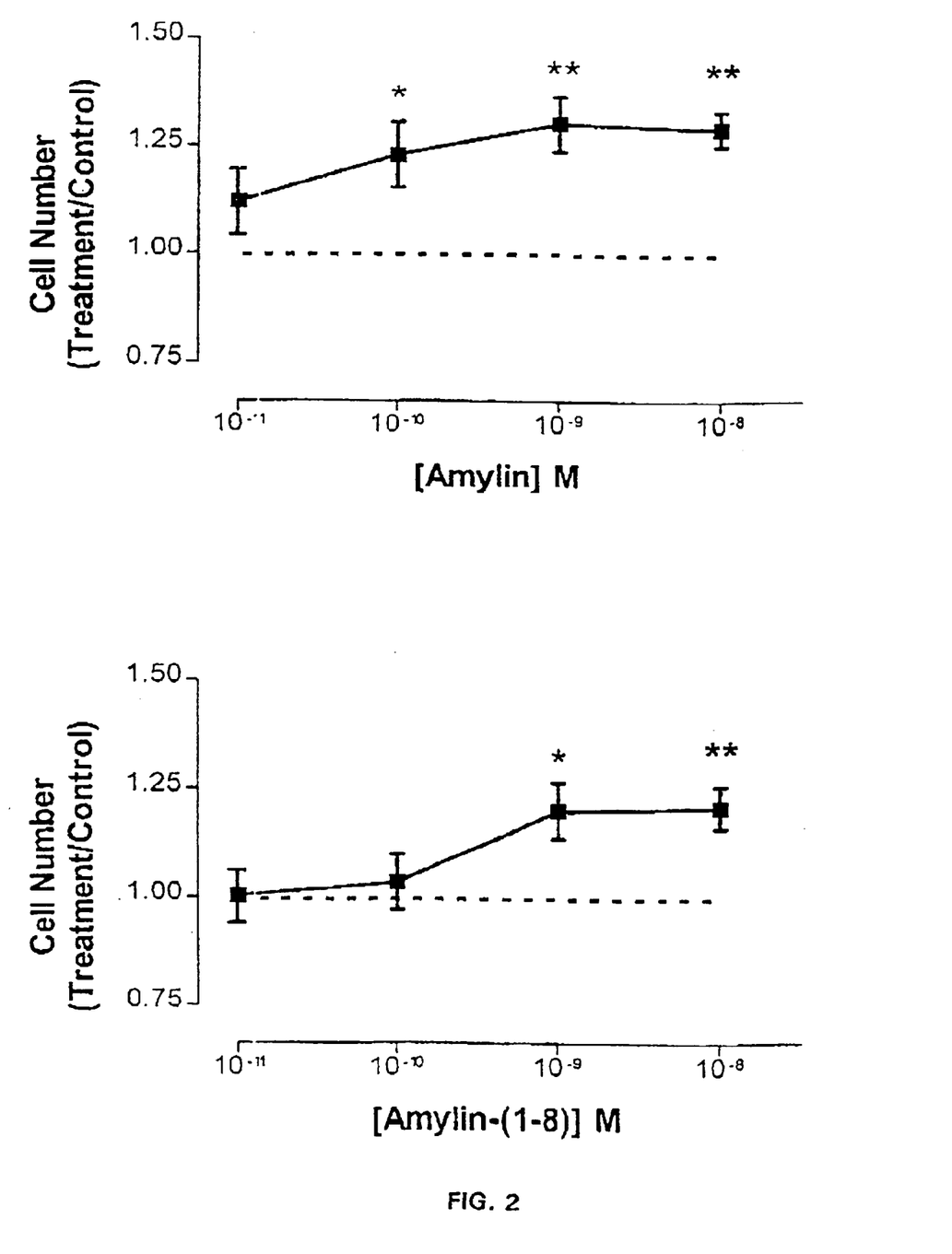
FIG. 2 Dose-response of rat amylin or rat amylin-(1–8) for 24 h on cell number in cultures of fetal rat osteoblasts. Data are expressed as a ratio of treatment to control. Data are mean"sem.*=significantly different from control, $p<0.03$;**$p<0.003$.
Figure 3:
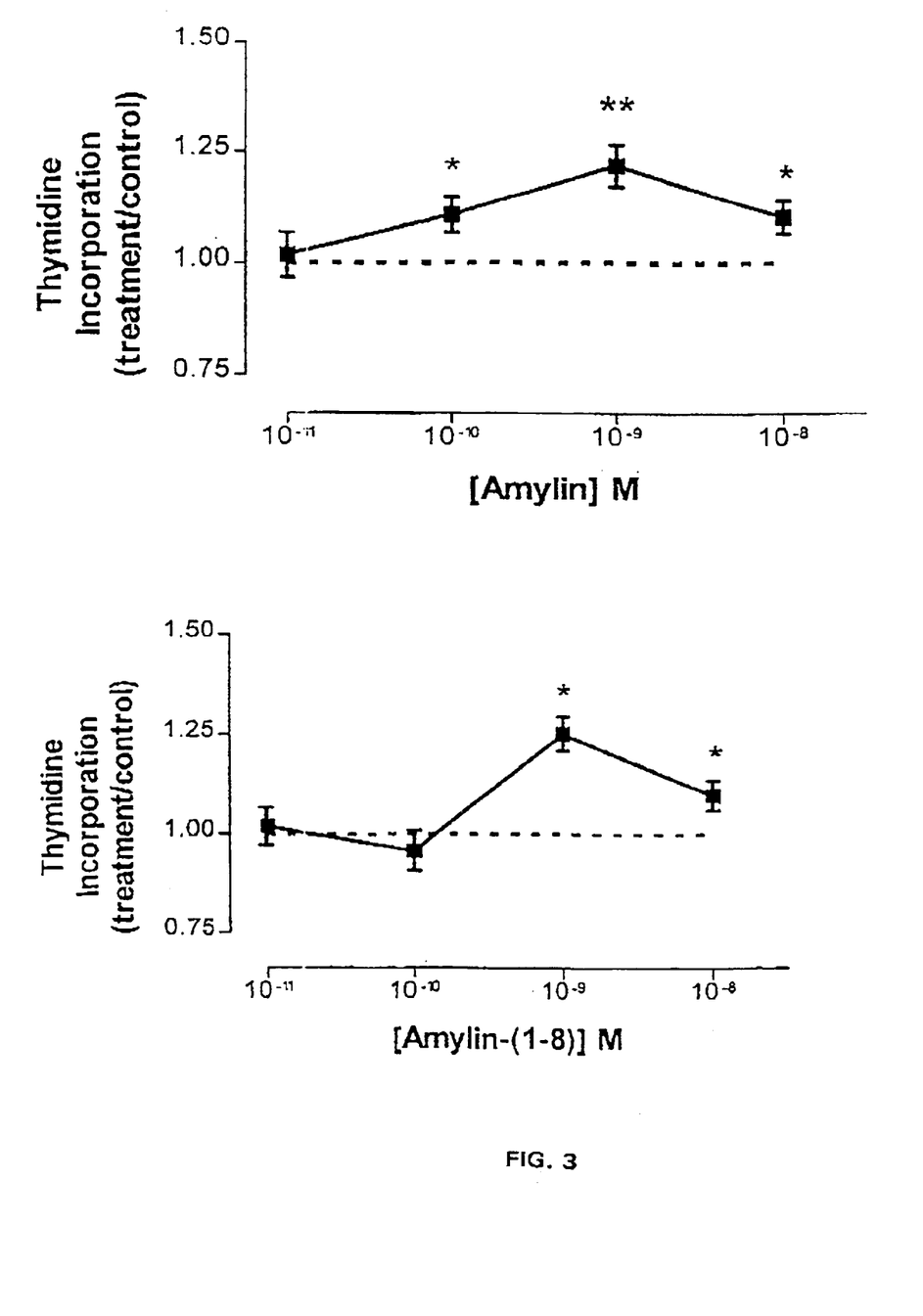
FIG. 3 Dose-response of rat amylin (upper panel) and rat amylin-(1–8) (lower panel) for 24h on thymidine incorporation in cultures of fetal rate osteoblasts. Data are expressed as a ratio of treatment to control. Data are mean"sem.*=significantly different from control, $p<0.03$;**$p<0.003$.

The dose-response relationships for action of intact amylin and amylin-(1–8) on cell number are shown in FIG. 2. The full molecule caused significant increases in cell number at concentrations of $10^{-10}$M and greater, the half-maximally effective concentration being $2.0 \times 10^{-11}$M. The maximal effect produced by amylin-(1–8) was not significantly less than that produced by the intact molecule but was only seen at concentrations of $10^{-9}$M and greater, and the half-maximal concentration was $2.4 \times 10^{-10}$M. Comparable results were seen in the actions of two peptides on thymidine incorporation into osteoblastic cells (FIG. 3).

Figure 4:
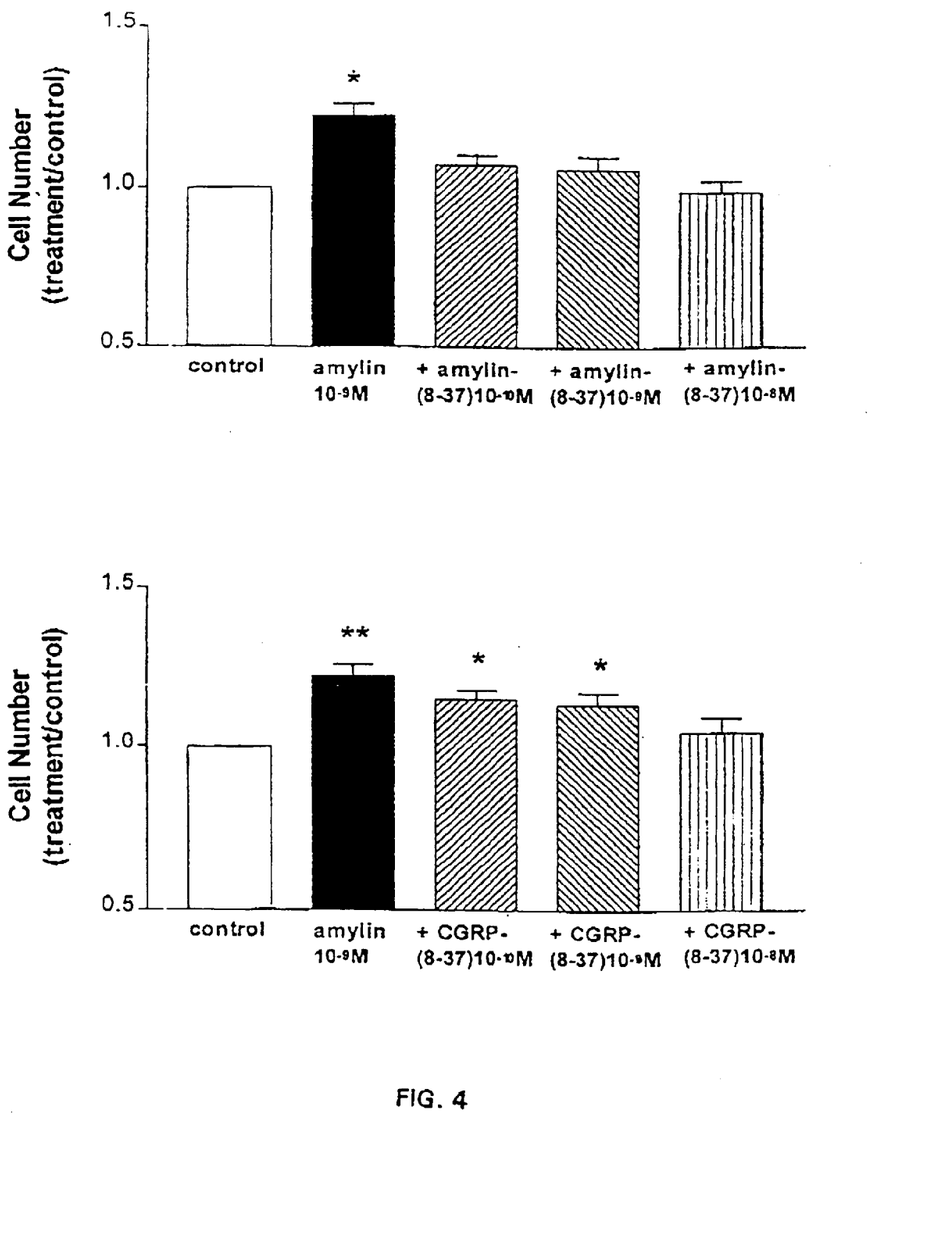
FIG. 4 Effect of rat amylin-(8–37) on amylin action on cell number in fetal rat osteoblasts (upper panel). Data are expressed as a ratio of treatment to control. Data are mean"sem.*=significantly different from control, $p<0.001$. Lower panel shows comparable data for rat CGRP-(8-37) .*=significantly different from control, $p<0.01$; **$p<0.001$.
Figure 5:
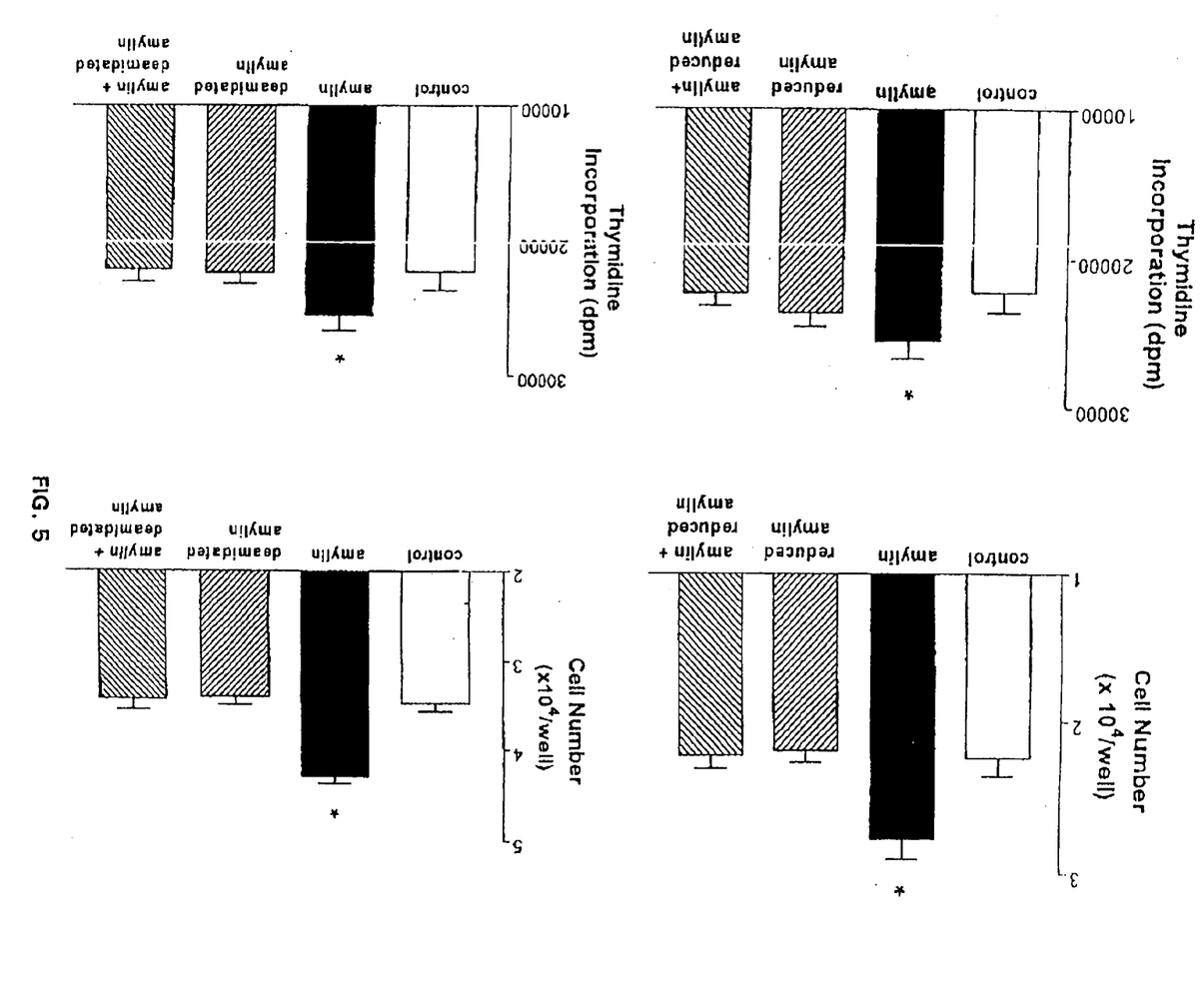
FIG. 5 Effect of reduced rat amylin and de-amidated rat amylin on amylin action on cell number and thymidine incorporation in fetal rat osteoblasts. All peptides were at a concentration of $10^{-9}$M. Data are mean"sem.*=significantly different from control, $p<0.001$.

Amylin-(8–37) functions as an amylin antagonist in other tissues so its effects on amylin-stimulated osteoblast proliferation were examined in this model (FIG. 4). Amylin-(8–37) in concentrations of $10^{-10}$M or greater completely blocked the proliferative effect of intact amylin ($10^{-9}$M). The comparable peptide fragment from CGRP also blocked the action of amylin, but this blockade was only complete at CGRP-(8–37) concentrations $>10^{-8}$M. Similar results with both blockers were seen for thymidine incorporation (data not shown). Two of the other amylin analogs studied, deamidated amylin and reduced amylin, were also effective blockers of the action of the intact peptide on cell number and thymidine incorporation, when present in equimolar concentrations (FIG. 5). In a similar manner, reduced amylin (1–8) was an effective blocker of the intact peptide on both cell number and thymidine incorporation.

The effects of these amylin antagonists on the action,s of amylin-(1–8) were also assessed (Table 1). Amylin-(1–8) consistently stimulated both cell number and thymidine incorporation, and its effects were blocked by equimolar concentrations of all the antagonists. Similarly, reduced amylin (1–8) was an effective blocker of amylin (1–8) at equimolar concentrations.

Bone Resorption

Figure 6:
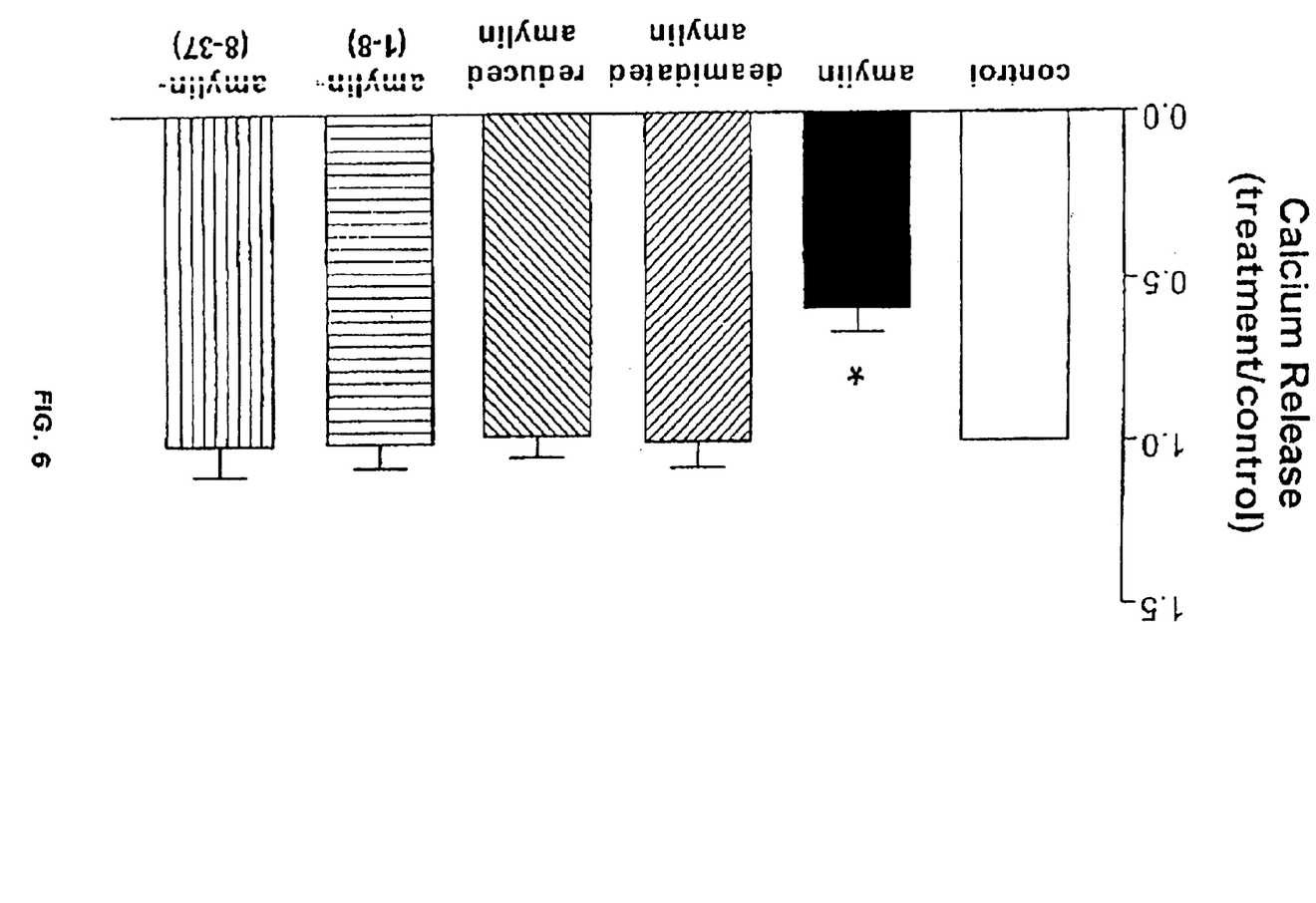
FIG. 6 Effect of equimolar concentrations ($10^{-8}$M) of rate amylin fragments on calcium release in bone organ culture. Data are expressed as a ratio of treatment to control. Data are mean"sem.*=significantly different from control, $p<0.001$.
Figure 7:
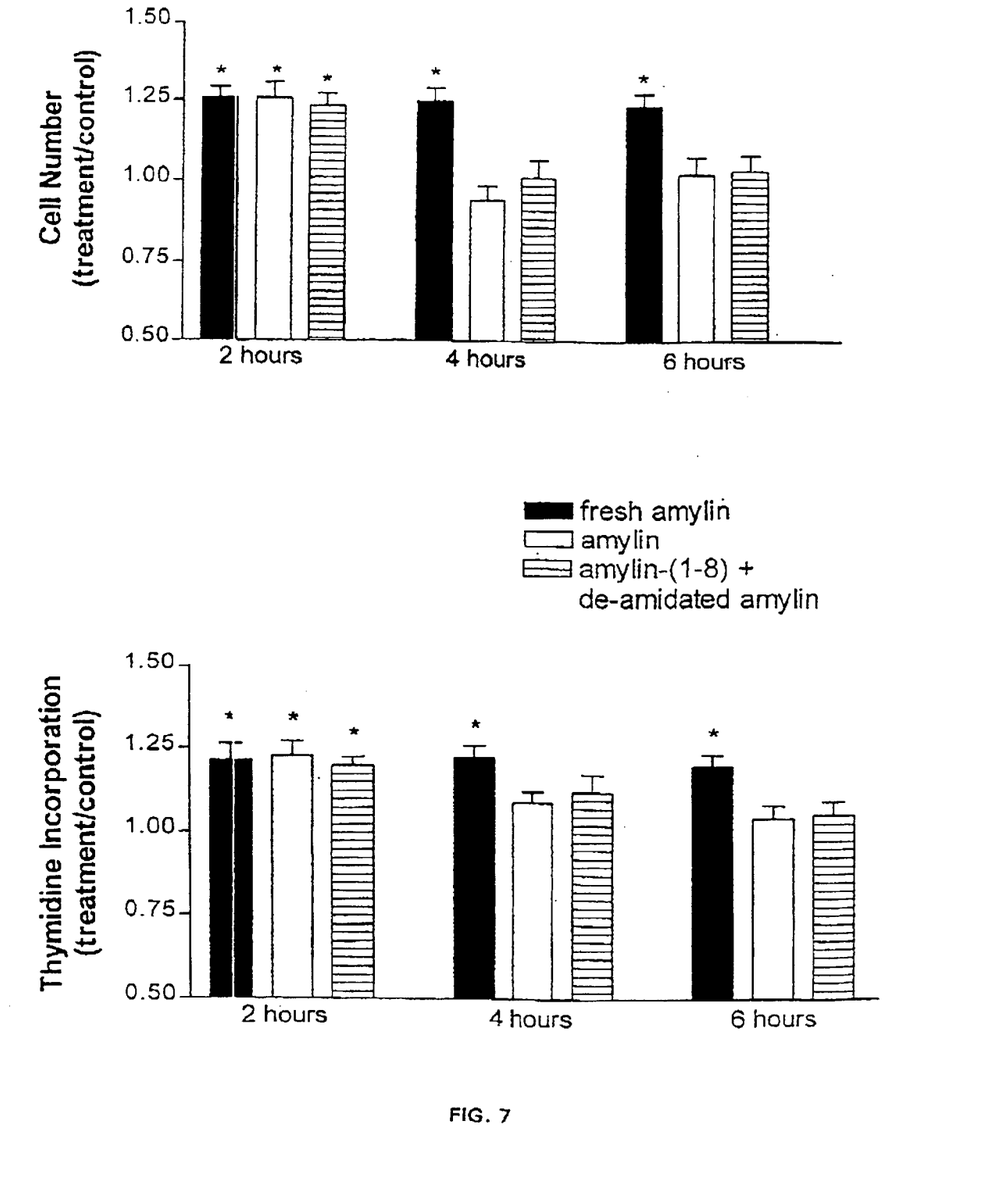
FIG. 7 Effect of intact amylin and amylin-(1–8) on cell number and thymidine incorporation in cultures of fetal rat osteoblasts following pre-incubation of each peptide in calvarial organ culture for the period indicated. Data are expressed as a ratio of treatment to control. Data are mean"sem.*=significantly different from control, p<0.001.

The effects of intact amylin and its four derivative peptides on bone resorption were assessed in cultures of neonatal mouse calvariae (FIG. 6). Amylin inhibited basal bone resorption (consistent with previously published results) but none of the other fragments had any effect on basal resorption. To determine whether this apparent lack of effect of amylin-(1–8) was attributable to its being catabolized more rapidly than intact amylin in the organ culture, the effect of pre-incubation in the organ culture on each peptide's osteoblast proliferative activity was assessed. In FIG. 7 it is shown that pre-incubation for two hours had no effect on the osteoblastic activity of either intact amylin or its (1–8) fragment, but that both peptides completely lost their activity if the pre-incubation lasted for four or more hours. This was true whether activity was assessed by cell number or by thymidine incorporation. Thus, both peptides appeared to be inactivated at comparable rates and their different effects on bone resorption cannot be accounted for by differential catabolism. This was consistent with the further finding that multiple additions of amylin-(1–8) (at 0, 8 and 30 hours) did not influence bone resorption (data not shown).

Figure 8:
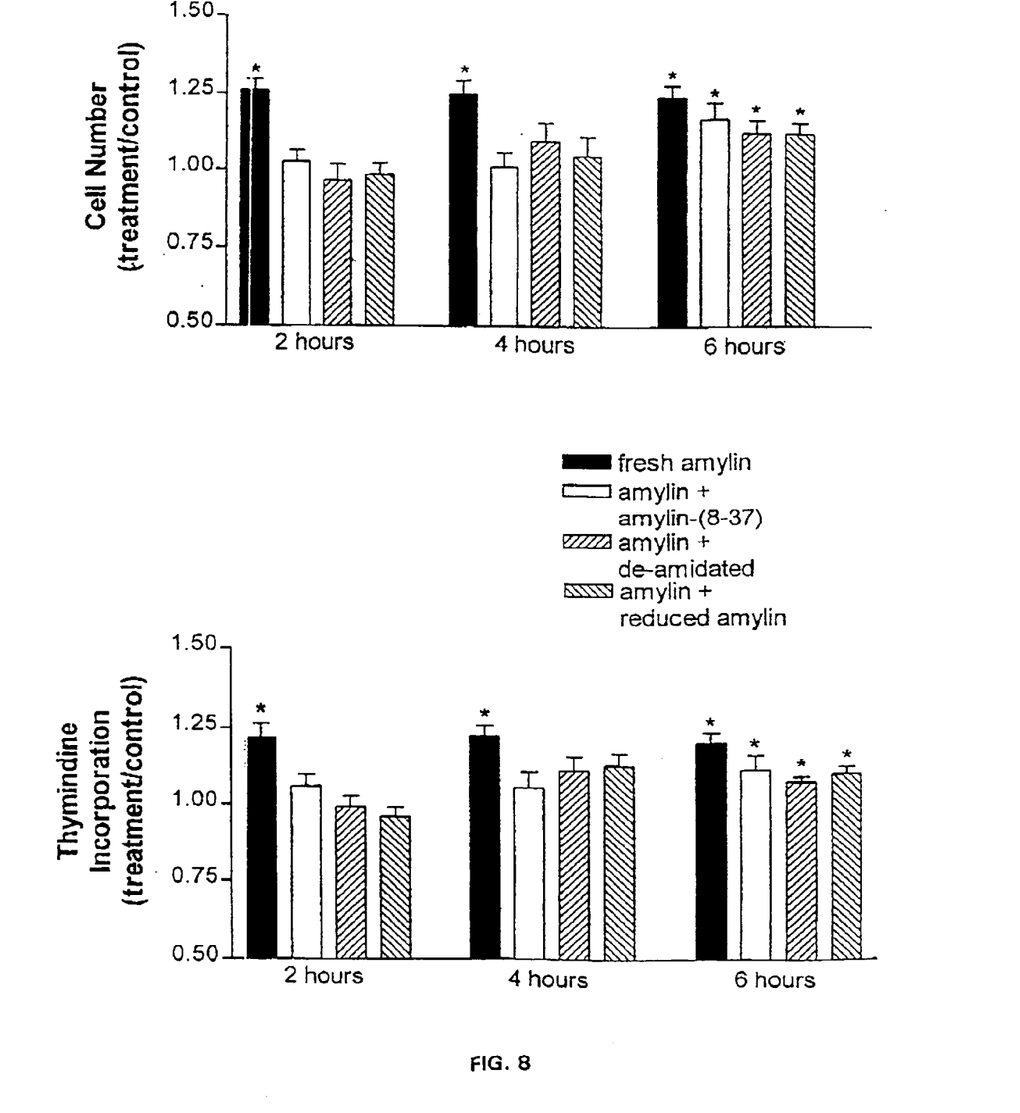
FIG. 8 Effect of equimolar concentrations ($10^{-9}$M) of rat amylin antagonists on cell number and thymidine incorporation in cultures of fetal rat osteoblasts following incubation in calvarial organ culture for the periods indicated. Data are expressed as a ratio of treatment to control and are mean"sem.*=significantly different from control ($p<0.05$).
Figure 9:
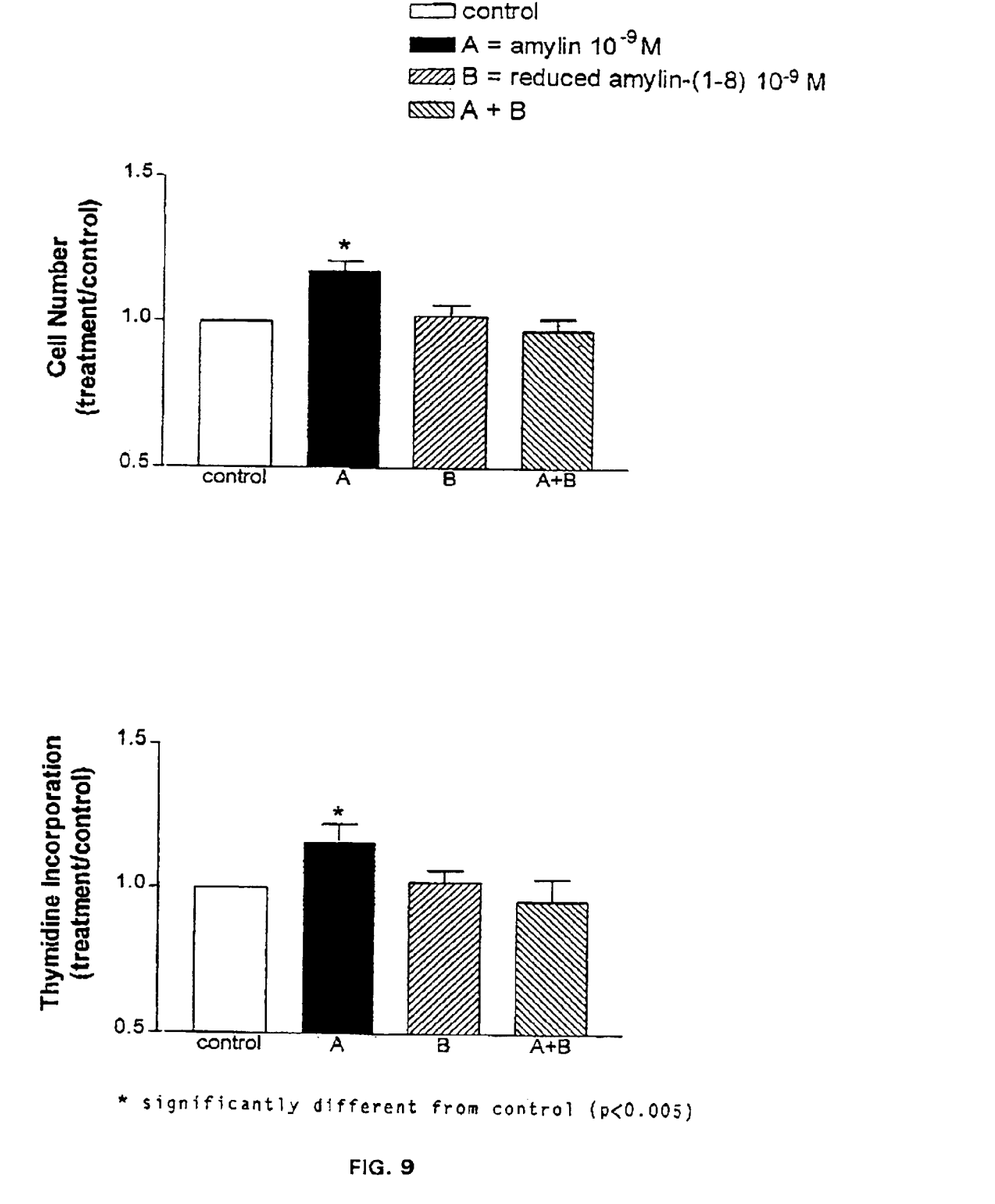
FIG. 9 Effect of equimolar concentrations ($10^{-9}$M) of intact amylin and reduced amylin (1–8) on cell number and thymidine incorporation in cultures of fetal rat osteoblasts. Data are expressed as a ratio of treatment to control and are mean"sem.*=significantly different from control (#0.005).

The actions of the antagonist peptides on amylin's inhibition of bone resorption are shown in Table 2. In contrast to the findings in osteoblasts, none of these peptides interfered with the reduction in bone resorption resulting from amylin treatment. Similarly, reduced amylin (1–8) did not act as a blocker in bone resorption. The rate of catabolism of these peptides in the calvarial culture was also assessed (FIG. 8). pre-incubation of amylin-(8–37), de-amidated amylin or reduced amylin with calvariae for six hours decreased their ability to block amylin's stimulation of osteoblast proliferation. This indicates that the breakdown of these antagonists is, if anything, slower than that of the native peptide (see FIG. 7). Thus the failure of these peptides to block amylin's effects on bone resorption in spite of their antagonism of its osteoblastic effects, is unlikely to result from their more rapid degradation in the bone organ culture model.

TABLE 1

INTERACTION OF AMYLIN-(1–8) AND AMYLIN BLOCKERS ON OSTEOBLAST PROLIFERATION

| {PRIVATE} Blocker | Control | Amylin-(1–8) | Blocker | Amylin + Blocker |
|---|---|---|---|---|
| {PRIVATE} Cell Number (×10⁴ cells/well) | | | | |
| Amylin-(8–37) | 4.83 " 0.06 | 5.85 " 0.21* | 4.80 " 0.08 | 4.83 " 0.12 |
| CGRP-(8–37) | 3.47 " 0.03 | 3.98 " 0.65* | 3.45 " 0.08 | 3.38 " 0.07 |
| Deamidated Amylin | 3.68 " 0.11 | 4.19 " 0.08* | 3.62 " 0.10 | 3.68 " 0.06 |
| Reduced Amylin | 3.97 " 0.11 | 4.68 " 0.08* | 3.90 " 0.16 | 3.98 " 0.10 |
| {PRIVATE} Thymidine Incorporation (dpm) | | | | |
| Amylin-(8–37) | 21366 " 964 | 26783 " 608** | 21669 " 784 | 23577 " 725 |
| CGRP-(8–37) | 21366 " 964 | 26788 " 611** | 20868 " 955 | 21125 " 725 |
| Deamidated Amylin | 22223 " 1376 | 25542 " 1127** | 22293 " 841 | 22060 " 912 |
| Reduced Amylin | 22223 " 1376 | 25550 " 1130** | 23621 " 955 | 22262 " 1060 |

Data are expressed as mean " sem
*significantly different from control (p#0.009)
**significantly different from control (p#0.0001)
All peptides were $10^{-9}$ M except for CGRP-(8–37), which was $10^{-8}$ M.

TABLE 2

INTERACTION OF AMYLIN AND ITS BLOCKERS ON BONE RESORPTION

| {PRIVATE} Blocker | Control | Amylin-(1–8) | Blocker | Amylin + Blocker |
|---|---|---|---|---|
| Amylin-(8–37) | 22.51 " 1.20 | 15.33 " 0.56** | 22.76 " 1.77 | 14.56 " 0.29* |
| CGRP-(8–37) | 25.15 " 1.22 | 13.23 " 0.65* | 22.22 " 2.04 | 14.29 " 1.36* |
| Deamidated Amylin | 26.80 " 1.99 | 15.87 " 0.30* | 26.78 " 0.96 | 17.47 " 0.69 |
| Reduced Amylin | 26.19 " 1.99 | 16.53 " 0.97* | 25.69 " 1.17 | 16.88 " 0.76* |

Data are % calcium released from bone in organ culture, expressed as mean " sem
*significantly different from control (p <0.001)
All peptides were $10^{-9}$ M except for CGRP-(8–37), which was $10^{-8}$ M.

The following examples illustrate the preparation of the compounds of this invention.

EXAMPLE 1

Boc-$N^e$-benzyloxycarbonyl-lysine-S-methybenzyl-cysteine-asparagine-O-benzyl-threonine-alanine-O-benzyl-threonine-S-methybenzyl-cysteine-alanine-benzhydrylamine resin.

Benzhydrylamine-polystyrene resin (Advanced ChemTech, Inc.) (1.2 g, 0.5 mmole) in the chloride ion form is placed in the reaction vessel of an Advanced ChemTech peptide synthesizer programmed to perform the following reaction cycle: (a) methylene chloride; (b) 33% trifluoroacetic acid in methylene chloride (2 times for 1 and 25 min each); (c) methylene chloride; (d) ethanol; (e) methylene chloride; (f) 10% triethylamine in chloroform.

The neutralized resin is stirred with Boc-alanine and diisopropylcarbodiimide (1.5 mmole each) in methylene chloride for 1 h and the resulting amino acid resin is then cycled through steps (a) to (g) in the above wash program. The following amino acids 1.5 mmole) are then coupled successively by the same procedure: Boc-S-methylbenzyl-Cys, Boc-O-benzyl-Thr, Boc-Ala, Boc-O-benzyl-Thr, Boc-Asn, Boc-S-methylbenzyl-Cys and Boc $N^e$benzyloxycarbonyl-Lys. After washing and drying, the completed resin weights 1.9 g.

EXAMPLE 2

Lysine-c[cysteine-asparagine-threonine-alanine-threonine-cysteine]-alanine-$NH_2$ (amino acid residues 1–8 of SEQ ID NO:1)

The resin described in Example 1 (1.9 g, 0.5 mmole) is mixed with anisole (5 ml), dithiothreitol (100 mg) and anhydrous hydrogen fluoride (35 ml) at $0_E$ C. and stirred for 45 min. Excess hydrogen fluoride is evaporated rapidly under a stream of dry nitrogen and free peptide precipitated and washed with ether. The crude peptide is then dissolved in 500 ml of 90% acetic acid to which is added a concentrated solution of $I_2$/MeOH until a permanent brown color is observed. Excess $I_2$ is removed by addition of ascorbic acid and the solution evaporated to a small volume which is applied to a column (2.5×90 cm) of Sephadex G-25 which is eluted with 50% AcOH. Fractions containing a major component by uv absorption and thin layer chromatography are then pooled, evaporated to a small volume and applied to a column (1.5×70 cm) of Vydac octadecylsilane silica (10.15 lm.) This is eluted with a linear gradient of acetonitrile in 0.1% trifluoroacetic acid in water. Fractions are examined by thin layer chromatography and analytical high performance liquid chromatography and pooled to give maximum purity. Repeated lyophilization of the solution from water gives the desired product as a white, fluffy powder (188 mg).

The product is found to be homogeneous by hplc and tlc. Amino acid analysis of an acid hydrolysate and MALD MS confirms the composition of the octapeptide.

We claim:

1. A method of treating a bone disorder, the method comprising stimulating osteoblast activity by administering an effective amount of a peptide of the formula Lys-Cys-Asn-Thr-Ala-Thr-Cys-Ala, wherein the carboxyl terminus of said peptide is amidated, or a salt of said peptide.

2. The method of claim 1, wherein osteoblast activity is stimulated without inhibiting bone resorption.

3. The method of claim 1, wherein the bone disorder is a bone fracture.

4. The method of claim 3, wherein osteoblast activity is stimulated without inhibiting bone resorption.

5. The method of claim 3, wherein the bone disorder is osteoporosis.

6. The method of claim 5, wherein osteoblast activity is stimulated without inhibiting bone resorption.

7. A method of ameliorating bone loss, the method comprising stimulating osteoblast activity by administering an effective amount of a peptide of the formula Lys-Cys-Asn-Thr-Ala-Thr-Cys-Ala, wherein the carboxyl terminus of said peptide is amidated, or a salt of said peptide.

8. The method of claim 7, wherein osteoblast activity is stimulated without inhibiting bone resorption.

9. The method of claim 7, wherein the method stimulates bone growth.

10. The method of claim 9, wherein osteoblast activity is stimulated without inhibiting bone resorption.

11. The method of claim 7, wherein the method increases or maintains bone density by prophylactic administration of the peptide or salt thereof.

12. The method of claim 11, wherein osteoblast activity is stimulated without inhibiting bone resorption.

13. The method of claim 7, wherein the method prevents bone deterioration.

14. The method of claim 13, wherein osteoblast activity is stimulated without inhibiting bone resorption.

15. The method of claim 7, wherein the method increases bone density.

16. The method of claim 15, wherein osteoblast activity is stimulated without inhibiting bone resorption.

17. The method of claim 7, wherein the method reverses bone loss.

18. The method of claim 17, wherein osteoblast activity is stimulated without inhibiting bone resorption.

19. A method of treating endocrine disorders, the method comprising stimulating osteoblast activity by administering an effective amount of a peptide of the formula Lys-Cys-Asn-Thr-Ala-Thr-Cys-Ala, wherein the carboxyl terminus of said peptide is amidated, or a salt of said peptide.

20. The method of claim 19, wherein osteoblast activity is stimulated without inhibiting bone resorption.

* * * * *

SEQUENCE LISTING

<160> NUMBER OF SEQ ID NOS: 2

<210> SEQ ID NO 1
<211> LENGTH: 37
<212> TYPE: PRT
<213> ORGANISM: Homo sapiens

<400> SEQUENCE: 1

Lys Cys Asn Thr Ala Thr Cys Ala Thr Gln Arg Leu Ala Asn Phe Leu
 1               5                  10                  15

Val His Ser Ser Asn Asn Phe Gly Ala Ile Leu Ser Ser Thr Asn Val
            20                  25                  30

Gly Ser Asn Thr Tyr
        35

-continued

```
<210> SEQ ID NO 2
<211> LENGTH: 8
<212> TYPE: PRT
<213> ORGANISM: Homo sapiens
<220> FEATURE:
<221> NAME/KEY: VARIANT
<222> LOCATION: 1
<223> OTHER INFORMATION: Xaa = Lys, or absent
<220> FEATURE:
<221> NAME/KEY: VARIANT
<222> LOCATION: 8
<223> OTHER INFORMATION: Xaa = Ala, or absent

<400> SEQUENCE: 2

Xaa Cys Asn Thr Ala Thr Cys Xaa
 1               5
```